(12) United States Patent
Reynolds, III et al.

(10) Patent No.: US 9,427,646 B2
(45) Date of Patent: Aug. 30, 2016

(54) LOWER LEG SENSING DEVICE AND METHOD OF PROVIDING DATA THEREFROM

(71) Applicants: Walter Arthur Reynolds, III, Haslett, MI (US); Brent M. Nowak, Ada, MI (US)

(72) Inventors: Walter Arthur Reynolds, III, Haslett, MI (US); Brent M. Nowak, Ada, MI (US)

( * ) Notice: Subject to any disclaimer, the term of this patent is extended or adjusted under 35 U.S.C. 154(b) by 0 days.

(21) Appl. No.: 14/834,372

(22) Filed: Aug. 24, 2015

(65) Prior Publication Data
US 2016/0051879 A1   Feb. 25, 2016

Related U.S. Application Data

(63) Continuation-in-part of application No. 13/859,196, filed on Apr. 9, 2013, now Pat. No. 9,114,296.

(51) Int. Cl.
| | |
|---|---|
| *A63B 23/04* | (2006.01) |
| *A63B 69/00* | (2006.01) |
| *G06K 9/00* | (2006.01) |
| *A61B 5/11* | (2006.01) |
| *A61B 5/00* | (2006.01) |
| *H04M 1/725* | (2006.01) |

(52) U.S. Cl.
CPC .......... *A63B 69/0028* (2013.01); *A61B 5/1121* (2013.01); *A61B 5/7415* (2013.01); *G06K 9/00342* (2013.01); *A61B 5/0002* (2013.01); *A61B 5/6828* (2013.01); *A61B 5/742* (2013.01); *A61B 5/7455* (2013.01); *A61B 2503/10* (2013.01); *A61B 2560/0223* (2013.01); *A63B 2220/16* (2013.01); *A63B 2220/89* (2013.01); *H04M 1/7253* (2013.01)

(58) Field of Classification Search
CPC ................... A63B 23/03508; A63B 23/0405; A63B 23/0494; A63B 24/0003; A63B 24/0006; A63B 24/0062
USPC ............................................... 482/8; 700/91
See application file for complete search history.

(56) References Cited

U.S. PATENT DOCUMENTS

| | | |
|---|---|---|
| 5,689,099 A | 11/1997 | Domburg |
| 9,114,296 B2 | 8/2015 | Reynolds, III |
| 2008/0248926 A1 | 10/2008 | Cole et al. |
| 2010/0184564 A1 | 7/2010 | Molyneux et al. |
| 2012/0130280 A1 | 5/2012 | Lee |

OTHER PUBLICATIONS

Milner, Clare E., et al, "Are knee mechanics during early stance related to tibial stress fracture in runners?", Clinical Biomechanics 22 (2007), pp. 697-703.

(Continued)

*Primary Examiner* — Allen Chan
(74) *Attorney, Agent, or Firm* — Harness, Dickey & Pierce, P.L.C.

(57) ABSTRACT

A lower leg sensing device includes a housing, a leg attachment member and real time data providing member. The housing includes a position angle sensor, an magnetic field sensor, and a foot contact sensor. The leg attachment member is configured to facilitate attachment of the housing to the lower leg of a user. The real-time data providing member provides data, in real-time, pertaining to the angle of a lower leg of a user relative to a line of gravity upon contact with an outside surface by a leg of a user. A method of providing data to a user that is running or walking is also disclosed.

12 Claims, 19 Drawing Sheets

(56) References Cited

OTHER PUBLICATIONS

Charry, Edgar et al., "Study on Estimation of Peak Ground Reaction Forces using Tibial Accelerations in Running", IEEE 978-1-4673-5499-8, Apr. 2-5, 2013, 6 pgs.

Hu, Wenzheng et al., "An Inertial Sensor System for Measurements of Tibia Angle with Applications to Knee Valgus/Varus Detection", IEEE 978-1-4799-2842-2, Apr. 21-24, 2014, 6 pgs.

Winfried, Vonstein, "Some reflections on maximum speed sprinting technique", New Studies in Athletics No. 2-3/1996, 5 pgs.

NPL document: "Apple iPhone 3G".

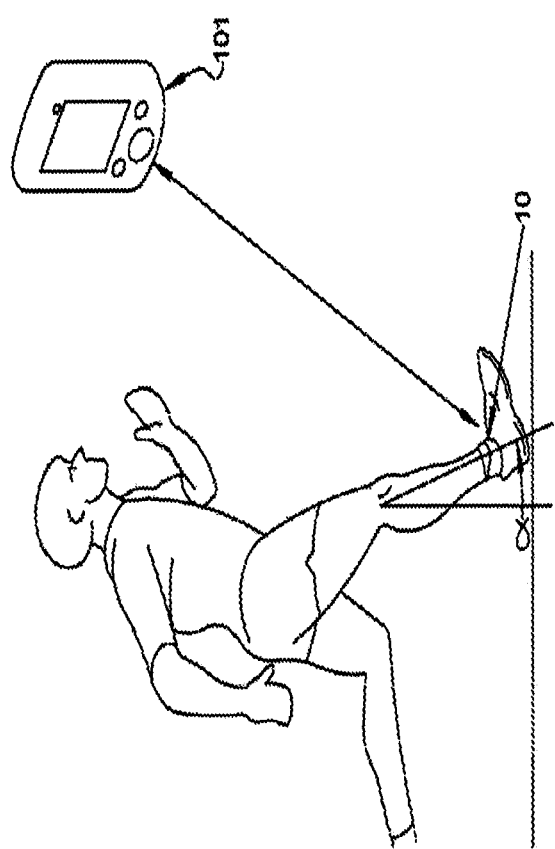

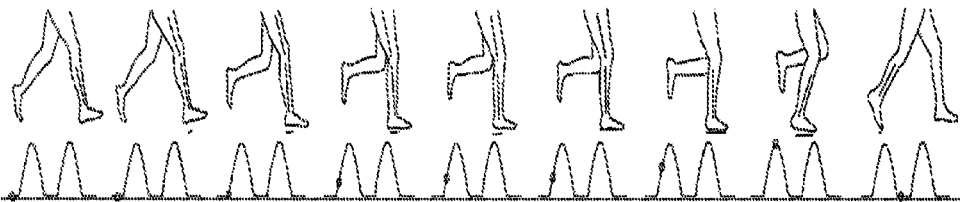
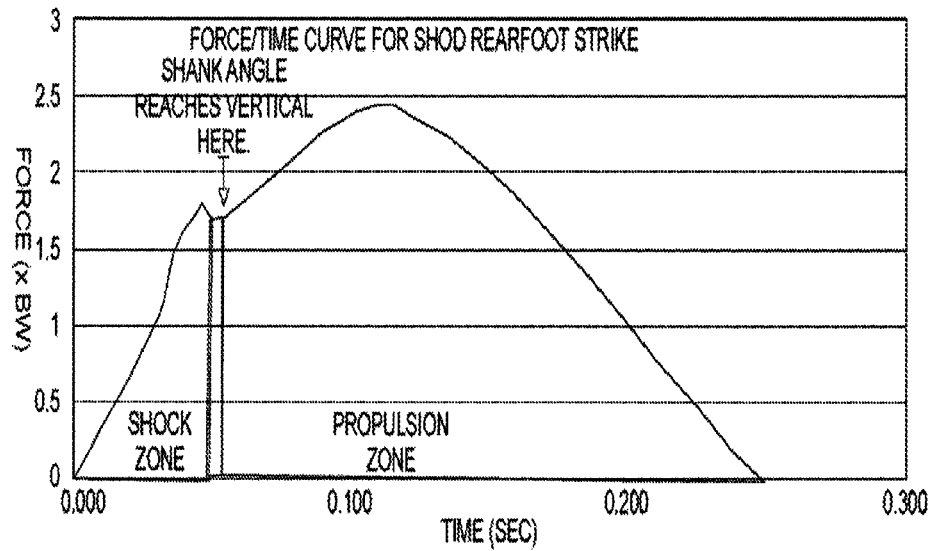
Fig 15

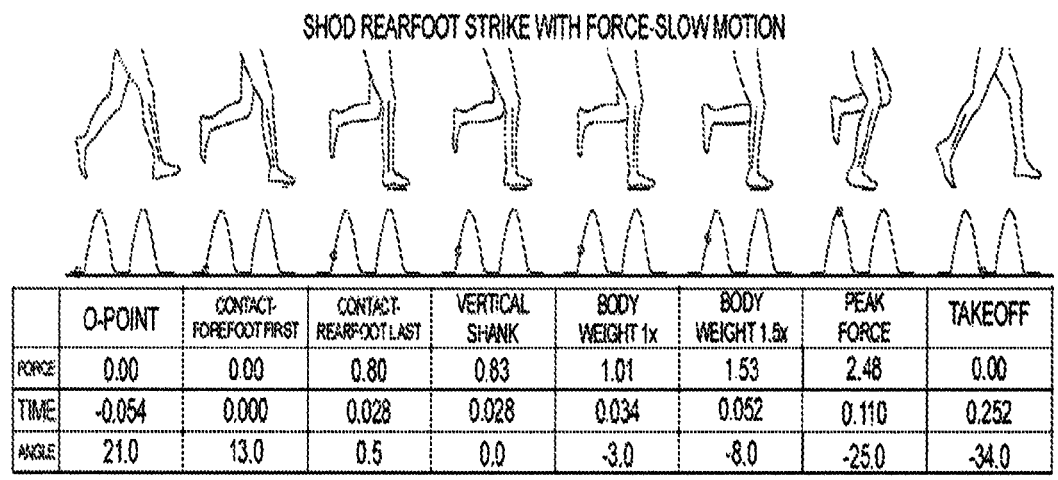
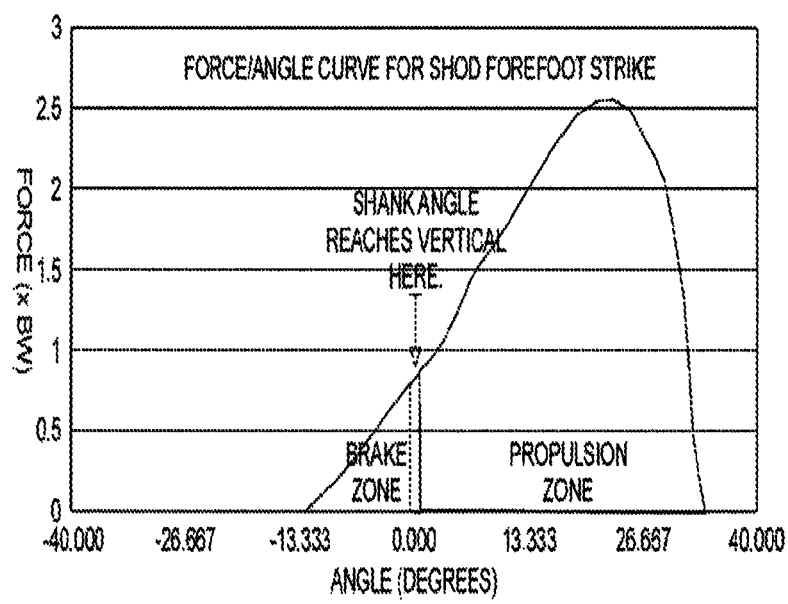
Fig 17

LOWER LEG SENSING DEVICE AND METHOD OF PROVIDING DATA THEREFROM

CROSS-REFERENCE TO RELATED APPLICATIONS

This application is a continuation-in-part of U.S. patent application Ser. No. 13/859,196 filed on Apr. 9, 2013. The entire disclosure of the above application is incorporated herein by reference.

FIELD

The invention relates in general to athletic training devices, and more particularly, to a lower leg angle sensing device which obtains data pertaining to a run or walk of a user, measuring, among other things, the angle of the lower leg when contacting the ground during activities such as running (i.e., the shank angle, as defined below).

BACKGROUND

Recreational and competitive walking and running are activities enjoyed by millions. It is estimated that there are over 112 million fitness walkers in the United States alone, along with almost 40 million runners. There is a constant desire among these groups to increase efficiency and performance while decreasing injury.

As a result, over the years, many advancements have appeared. Such advancements include advancements to equipment, namely, clothing and shoes. In the case of shoes, advancements have provided improved cushioning, improved stability and improved gate, as well as an improved level of comfort. Clothing has evolved high performance fabrics which provide sweat management techniques that enhance comfort and minimize skin irritation.

Other advancements have come in the form of training aids. Such advancements include heart rate monitors and the like. Such advancements assist by providing data pertaining to certain physical features (i.e., heart rate). One interesting advancement has been in the form of real-time providing of data. For example, with current heart rate devices, a user can be instantly advised as to current heart rate and can be alerted as to changes in the heart rate. The user is then able to make immediate changes and can watch to see what effect those changes have on the parameter that is being tracked.

Even with these improvements, there remains a need to further improve the efficiency and performance of walkers and runners, while reducing the instances of injury as well as the severity of injuries.

Thus, it is an object of the present disclosure to provide additional training aids to achieve improvements in efficiency and performance while reducing injury.

SUMMARY

The disclosure is directed to a method of providing data to a user that is running or walking comprising the steps of: providing a lower leg sensing device, the lower leg sensing device including at least a position angle sensor and a foot contact sensor; coupling the lower leg sensing device to a lower leg of a user; sampling the position angle sensor and the foot contact sensor; determining the angle of the lower leg relative to a line of gravity based upon the data received from the position angle sensor and the foot contact sensor; providing information to a user pertaining to the angle of the lower leg relative to the line of gravity.

In a preferred embodiment, the step of providing information to a user comprises the steps of: comparing the angle that has been determined to a known range of acceptable angles; and providing a user understandable signal to a user sufficient for the user to determine whether the angle that has been determined is within the known range of acceptable angles.

In another preferred embodiment, the step of providing comprises the steps of: providing a first user understandable signal if the angle that has been determined is within the known range of acceptable angles; providing a second user understandable signal if the angle that has been determined is outside of the known range of acceptable angles on a first side of the range; and providing a third user understandable signal if the angle that has been determined is outside of the known range of acceptable angles on a second side of the range.

In another preferred embodiment, the first, second and third user understandable signals comprise at least one of audible, visual and kinesthetic signals.

In another preferred embodiment, the method further comprises the step of: providing a computing device that is separated from the sensing device; establishing a communication link between the computing device and the sensing device; and transmitting data obtained through sampling of the position angle sensor and the foot contact sensor.

In another preferred embodiment, the method further comprises the step of: displaying in real-time on the computing device the data obtained through sampling of the position angle sensor and the foot contact sensor.

In yet another preferred embodiment, the computing device comprises a smartphone coupled wirelessly to the sensing device, and the step of displaying comprises the step of displaying on a display of the smartphone.

In some such embodiments, the smartphone further includes a GPS sensor and further includes a clock, the method further comprising the steps of: computing at least one other parameter based upon the sensors, including, at least one of cadence, speed, time, stride length, and ground contact time.

In another embodiment, the lower leg sensing device further includes: a housing, wherein the position angle sensor and the foot contact sensor are positioned therewithin; and a leg attachment member configured to releasably attach the housing to the lower leg of the user.

In another embodiment, the leg attachment member comprises a strap that is configured to enable releasable attachment to the housing to an ankle region of the lower leg of the user.

In another aspect of the disclosure, the disclosure is directed to a lower leg sensing device comprising a housing and a leg attachment member and a real-time data providing means. The housing has a position angle sensor and a foot contact sensor. The leg attachment member is configured to facilitate attachment of the housing to the lower leg of a user. The real-time data providing means provides data pertaining to the angle of a lower leg of a user relative to a line of gravity upon contact with an outside surface by a leg of a user.

In a preferred embodiment, the providing means further comprises a computing device and a signal member. The computing device is wirelessly coupled to the position angle sensor and the foot contact sensor. The signal member is coupled to the computing device. The signal member is capable of providing a user understandable signal.

In another preferred embodiment, the user understandable signal may be any one of audible, visual and kinesthetic signals. Such signals may likewise include silence.

In another preferred embodiment, the computing device further comprises a smartphone wherein the signal member comprises at least one of the display of the smartphone, a speaker of the smartphone and a vibration mechanism of a smartphone.

DRAWINGS

The disclosure will now be described with reference to the drawings wherein:

FIG. 1 of the drawings is a schematic representation of the device of the present disclosure, showing, in particular, communication thereof with an outside device;

FIG. 2 of the drawings is a partial perspective view of the device coupled to a leg of a user;

FIG. 3 of the drawings is a schematic composite view of the device of the present disclosure, showing, in particular, the incorporation of the housing within the leg attachment member;

FIG. 4 of the drawings is a plurality of screenshots from a computing device electronically coupled to the device, showing, in particular, the calibration of the device for a particular user;

FIG. 5 of the drawings is a plurality of screenshots from a computing device electronically coupled to the device, showing, in particular, real-time feedback of various parameters and data pertaining to a current use by a user, such information including the distance traveled, the time utilized, leg angle, cadence, pace, and an overall "smart score" which corresponds to an algorithm that provides a grade for the current activity;

FIG. 6 of the drawings is a plurality of screenshots from a computing device electronically coupled to the device, showing, in particular, summaries of past exercise routines as well as information pertaining to each, including the overall "smart score" that has been determined through analysis of all of the prior activities (or a predetermined portion of the same). Additionally, options to export the results to social media and to otherwise share (i.e., through email) are provided;

FIG. 7 of the drawings is a schematic representation of a computing device of the present disclosure;

FIG. 8 a schematic of the system according to the present teachings having magnetometer and accelerometer;

FIG. 15 represents the stride of a third user having a rearfoot strike;

FIG. 17 represents force vs. time data for the stride of a user having a forefoot strike;

DETAILED DESCRIPTION OF THE DISCLOSURE

Figure 3:
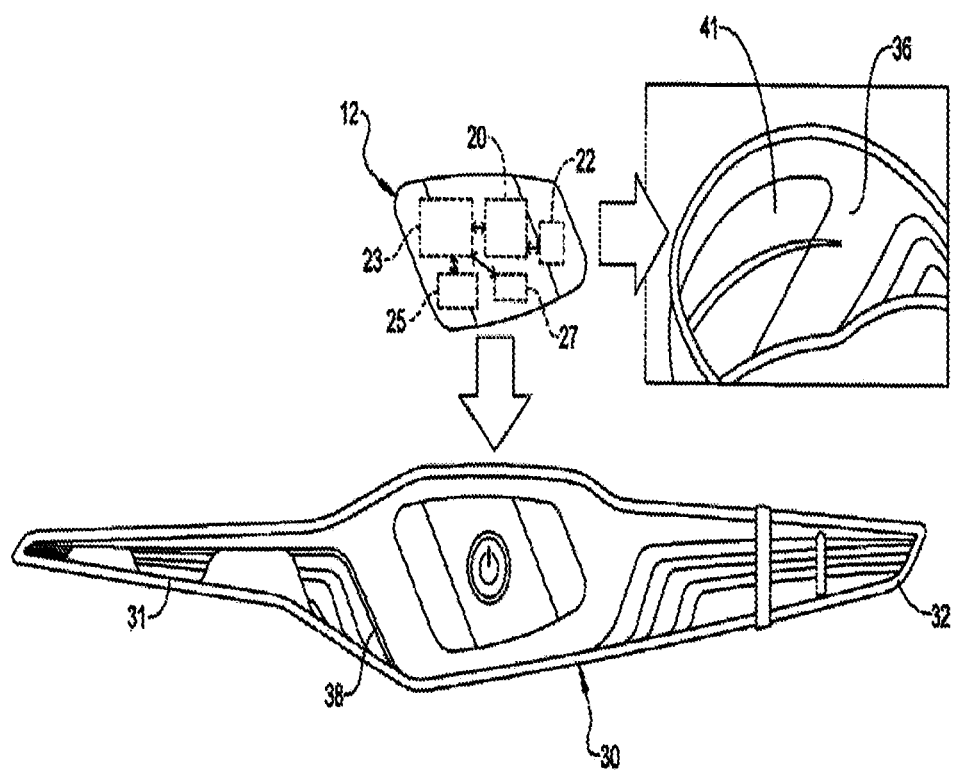

While this invention is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Referring now to the drawings and in particular to FIG. 1, the lower leg sensing device is shown generally at 10. The sensing device is configured to interface with an outside computing device, such as smartphone 101. It will be understood that the outside computing device may comprise any one or more of a general purpose computer, tablet computer, smartphone, PDA, smart watch, special purpose computing device, among others. Thus, while in the disclosure below, reference will be made to smartphone 101, with the understanding that a number of other devices are likewise contemplated for use. Details pertaining to the computing device are described in the following paragraphs.

It will be understood that although not required, aspects of the descriptions below will be provided in the general context of computer-executable instructions, such as program modules, being executed by a computing device, sensing device alone or in cooperation with other remote computing devices through outside communication (which will also be described).

More specifically, aspects of the description below will reference acts, methods and symbolic representations of operations that are performed by one or more computing devices or peripherals, unless indicated otherwise. As such, it will be understood that such acts and operations, which are at times referred to as being computer-executed, include the manipulation by a processing unit of electrical signals representing data in a structured form. This manipulation transforms the data or maintains it at locations in memory, which reconfigures or otherwise alters the operation of the computing device or peripherals in a manner well understood by those skilled in the art. The data structures where data is maintained are physical locations that have particular properties defined by the format of the data.

Generally, program modules include routines, programs, objects, components, data structures, and the like that perform particular tasks or implement particular abstract data types. Moreover, those skilled in the art will appreciate that the computing devices need not be limited to a specialized control module within the housing of the device, or conventional personal computers, and include other computing configurations, including hand-held devices (i.e., smartphones), multi-processor systems, microprocessor based or programmable consumer electronics, network PCs, mini-computers, mainframe computers, and the like. Similarly, the computing devices need not be limited to a stand-alone computing device, as the mechanisms may also be practiced in distributed computing environments linked through a communications network. In a distributed computing environment, program modules may be located in both local and remote memory storage devices.

Figure 7:
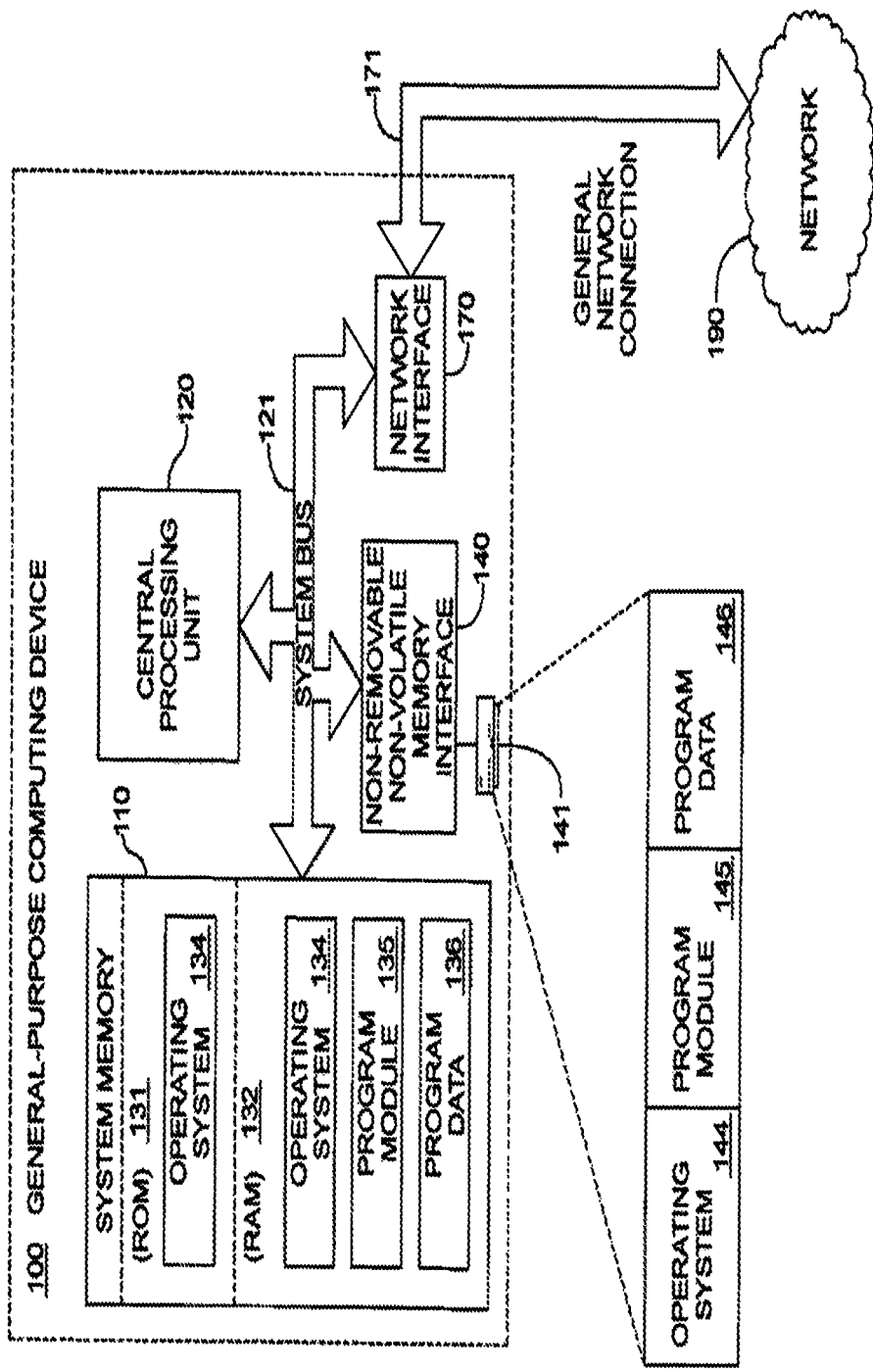

With reference to FIG. 7, an exemplary general-purpose computing device is illustrated in the form of the exemplary general-purpose computing device 100. The general-purpose computing device 100 may be of the type utilized for the device 10 or for the outside computing devices 101 (FIG. 1) as well as the other computing devices which may comprise the outside computing device servers with which communication can be established. As such, it will be described with the understanding that variations can be made thereto. The exemplary general-purpose computing device 100 can include, but is not limited to, one or more central processing units (CPUs) 120, a system memory 130 and a system bus 121 that couples various system components including the system memory to the processing unit 120. The system bus 121 may be any of several types of bus structures including a memory bus or memory controller, a peripheral bus, and a local bus using any of a variety of bus architectures. Depending on the specific physical implementation, one or more of the CPUs 120, the system memory 130 and other components of the general-purpose computing device 100 can be physically co-located, such as on a single chip. In such a case, some or all of the system bus 121 can be nothing more than communicational pathways within a single chip structure and its illustration in FIG. 3 can be nothing more than notational convenience for the purpose of illustration.

The general-purpose computing device 100 also typically includes computer readable media, which can include any available media that can be accessed by computing device 100. By way of example, and not limitation, computer readable media may comprise computer storage media and communication media. Computer storage media includes media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the general-purpose computing device 100. Communication media typically embodies computer readable instructions, data structures, program modules or other data in a modulated data signal such as a carrier wave or other transport mechanism and includes any information delivery media. By way of example, and not limitation, communication media includes wired media such as a wired network or direct-wired connection, and wireless media such as acoustic, RF, infrared, Bluetooth and other wireless media. Combinations of the any of the above should also be included within the scope of computer readable media.

When using communication media, the general-purpose computing device 100 may operate in a networked environment via logical connections to one or more remote computers. The logical connection depicted in FIG. 1 is a general network connection 171 to the network 190, which can be a local area network (LAN), a wide area network (WAN) such as the Internet, or other networks. The computing device 100 is connected to the general network connection 171 through a network interface or adapter 170 that is, in turn, connected to the system bus 121. In a networked environment, program modules depicted relative to the general-purpose computing device 100, or portions or peripherals thereof, may be stored in the memory of one or more other computing devices that are communicatively coupled to the general-purpose computing device 100 through the general network connection 171. It will be appreciated that the network connections shown are exemplary and other means of establishing a communications link between computing devices may be used.

The general-purpose computing device 100 may also include other removable/non-removable, volatile/nonvolatile computer storage media. By way of example only, FIG. 1 illustrates a hard disk drive 141 that reads from or writes to non-removable, nonvolatile media. Other removable/non-removable, volatile/nonvolatile computer storage media that can be used with the exemplary computing device include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140.

The drives and their associated computer storage media discussed above and illustrated in FIG. 3, provide storage of computer readable instructions, data structures, program modules and other data for the general-purpose computing device 100. In FIG. 1, for example, hard disk drive 141 is illustrated as storing operating system 144, other program modules 145, and program data 146. Note that these components can either be the same as or different from operating system 134, other program modules 135 and program data 136. Operating system 144, other program modules 145 and program data 146 are given different numbers here to illustrate that, at a minimum, they are different copies.

Referring again to FIG. 1, the lower leg sensing device 10 is configured to, primarily, sense the location of the foot relative to the pavement, and, simultaneously, the lower leg angle (commonly referred to as the shank angle). More particularly, the lower leg angle is the angle of the lower leg relative to vertical at the moment of ground contact (with vertical being the direction of the force vector of gravity extending through the center of the knee). The angle is generally defined by a mid-coronal line extending from the center of the knee joint (lateral side) through the central of the lateral malleolus). Thus, it will be understood that vertical corresponds to a line extending through the center of the knee joint (lateral side) and in the direction of the force vector of gravity (commonly referred to as the line of gravity). Additionally, reference to lower leg angle, herein, refers to the shank angle as defined. Advantageously, with such information, angular velocity of the lower leg, ground contact time of the foot, running speed, step cadence, ground impact transient and lower leg position can be tracked. Furthermore, information can be provided to the user to aid the user in making adjustments to his/her running gate. Such improvement leads to improved form, and speed, with a reduction in injury propensity.

With reference to FIG. 2, the lower leg sensing device 10 includes housing 12 and leg attachment member 14. The housing 12 includes a cavity within which a computing device 23, including some of the components identified above (such as an outside communication portion 27, can be positioned. To the computing device, a plurality of sensors can be coupled. The plurality of sensors include a position angle sensor 20 and a foot contact sensor 22. The housing 12 may comprise a plurality of components which are coupled together to form the cavity. Additionally, the housing can have an accommodation for a power source 25, such as a rechargeable battery, a disposable battery or the like.

As to the sensors, the position angle sensor 20 comprises a sensor that can determine an angular position relative to a known angular position, or a sensor that can sense a change in angular position. Such sensors are known to those of skill in the art. The foot contact sensor comprises an accelerometer. Such a sensor is likewise known in the art. Such a sensor can sense the change in acceleration (and in turn position or velocity). An on/off switch, as well as an audible signal generator (speaker, piezoelectric element) can also be included (or a visual signal, such as an LED, or a kinesthetic signal, such as a vibrating element).

The leg attachment member 14 is shown as comprising band 30. The band 30 includes a first end 31 and a second end 32, an inner surface 36 and an outer surface 38. An attachment member couples the first end to the second end to make a hoop that can be installed to extend about the leg of a user. In an embodiment, the hook and loop portion may be on the first end, with a ring at the second end. The first end is inserted through the ring at the second end and then folded over itself so as to couple the hook and loop portions together. In the embodiment shown, the attachment member comprises a hook and loop fastener, wherein a first component is coupled to the first end and a second component is coupled to the second end. In the embodiment shown, the housing can be inserted into a pocket 41 that is created within the band 30. In such an embodiment, a slit may be disposed on the inner surface 36, and may provide access to the pocket. In another embodiment, the housing is coupled to the outside surface of the band 30. In other embodiments, the band 30 may be co-molded with a portion of the housing, so as to appear as a single integrally formed member.

In operation, the user first straps the sensing device 10 to his or her leg. The user insures that the power source (i.e., battery) is properly installed and that there is power to the various components. Once positioned, the user can adjust position and retention of the band to insure that the device remains stationary on the leg of the user.

Once fully installed, the position angle sensor can be calibrated. It is contemplated that the position angle sensor is calibrated to set a baseline position. For example, the position angle sensor can be calibrated so that the initial resting position (wherein the lower leg of the user is substantially vertical) is defined. To set a baseline position, a button may be disposed on the device which may be pressed, after which the user can position the foot vertically for a period of time (which time can be announced by the device through audible tones, vibrations or the like).

Once calibrated, the device can be activated so as to begin logging (which again can be achieved through a button disposed on the device). As the user runs, the two sensors can be sampled at a predetermined rate. For example, each of the sensors can be sampled at 1000, 10,000, 1000,000 Hz, 1 MHz, etc. Of course, this is exemplary only, and it is contemplated that any number of sampling rates could be employed, with the understanding that the slower the sampling rate, the less data/accuracy is achieved, whereas the faster the sampling rate, the more data that is obtained.

Among other data, the system can log data with respect to time. Thus, at each sampling, the data pertaining to the position angle and the data pertaining to the foot contact sensor is read and stored. In such an embodiment, the data can be stored in volatile and/or nonvolatile memory. In some embodiments, a provision can be made for a removable storage medium (i.e., a memory card, such as a microSD card, or the like). When the user is done logging information, a button can be pressed to stop the recording of data.

It will be understood that the device may provide some level of processing of the information that is received from the sensors. For example, as the user runs, the foot having the sensor proceeds up and down with each running stride. When the foot of the user hits the ground, further downward movement stops (i.e., the foot experiences a high rate of deceleration). Conversely, when the foot leaves the ground, the foot experiences an elevated rate of acceleration. Thus, it can be determined, based on the data from the foot contact sensor, when the foot hits the ground and when the foot releases from the ground.

Thus, to determine the shank angle, a (FIG. 1) when contact with the ground is achieved, it is necessary to obtain the angular position of the lower leg relative to the line of gravity when there is an abrupt deceleration of the foot sensed by the foot contact sensor.

It is known that the angular disposition of the lower leg when the foot contacts the ground should be close to matching the line of gravity. Such a position has been found to define the proper running form, as such a position enhances efficiency and reduces injury. Thus, the data obtained from these sensors can provide the precise angle of the lower leg upon impact of the foot with the ground.

With additional processing, it is possible to provide real-time feedback to the user relative to the shank angle. For example, if the lower leg is within the proper range (i.e., vertical+/−5 degree), a first audible signal can be emitted. If the lower leg is too far from vertical (i.e., the line of gravity) in either direction, a second audible signal can be emitted. Additionally, two different second audible signals can be transmitted, one if the lower leg is too far from vertical in one direction, and a second if the lower leg is too far from vertical in the other direction. It will also be understood that the signal to the user may be in a form other than audible. For example, such signals may comprise audible, visual and kinesthetic signals. In other words, a visual feedback may be provided, such as a flashing light, or a kinesthetic signal, such as a vibration. Additionally, it is contemplated that combinations of signals may be utilized. It is also contemplated that the first audible signal (or other signal) can be silence or no signal at all. Such lack of any signal, it will be understood, corresponds to a condition wherein the activity is proceeding within all proper parameters.

This means for providing real-time data pertaining to the angle of a lower leg of a user relative to the line of gravity upon contact with an outside surface by a leg of a user provides information that the user could not otherwise obtain—it is virtually impossible to determine the angle of the lower leg with any precision on someone else while running, much less on oneself when running Thus, real-time analysis has not been possible as to lower leg angle. Moreover, the user can attempt to make adjustments, and receive feedback in a real-time manner as to the effectiveness of these adjustments.

In other embodiments, and in most preferred embodiments, the device can be configured to interface with a smartphone 101 on a real-time basis, wherein the features, calibrations, and settings are all set from an application within the smartphone 101. For example, the device can be configured to communicate with the smartphone 101 first. Any number of different protocols are contemplated, as identified above with respect to the computing device. Additionally, other short range protocols are likewise contemplated, including by not limited to WIFI, zigbee, cellular, Bluetooth, RF and the like. One particular embodiment takes advantage of the low power Bluetooth protocol found in Bluetooth 4.0 specification. Of course, the device is not limited to any particular type of communication protocol. It is also contemplated that a wired solution may be employed in certain embodiments, such as a USB communication protocol or the like.

In such embodiments, the data obtained through the sensors can be transmitted real-time to the smartphone. The smartphone includes a program that can calculate any number of different parameters from the data received, and, optionally provide some sensors of its own (i.e., GPS, clock, among others). Thus, the cell phone can initiate the audible signals contemplated above that correspond to the particular angle of the lower leg of the user. Additionally, the communication relative to calibration, resetting, data purging, among others can all be controlled from the smartphone. The smartphone can also compile the data and store the data.

It is contemplated that the data that is gathered can be transmitted to an outside server for further analysis. Such analysis may include the application of certain algorithms to the data to determine patterns, and to also prescribe certain training regimen. In addition, problematic conditions can be determined prior to such conditions becoming a problem.

Figure 4:
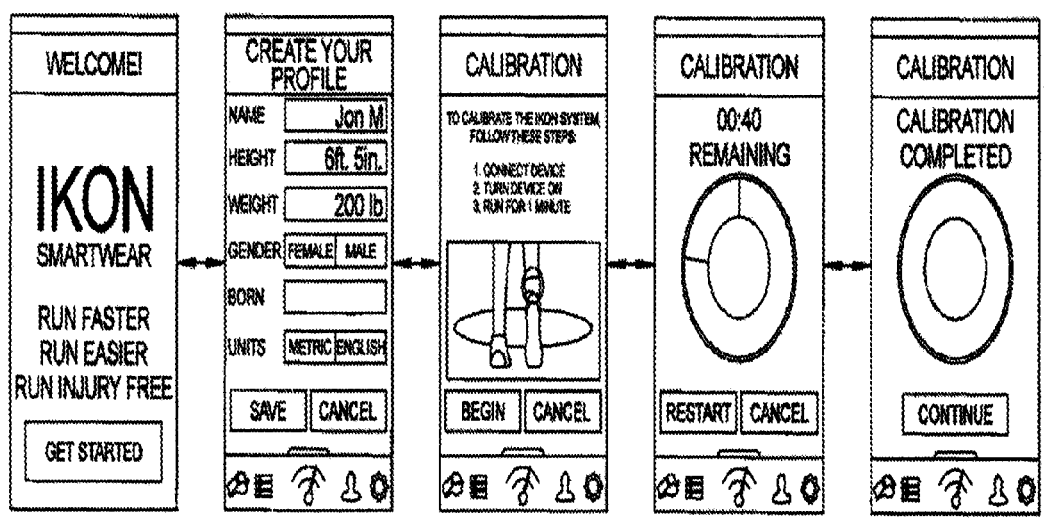
Figure 5:
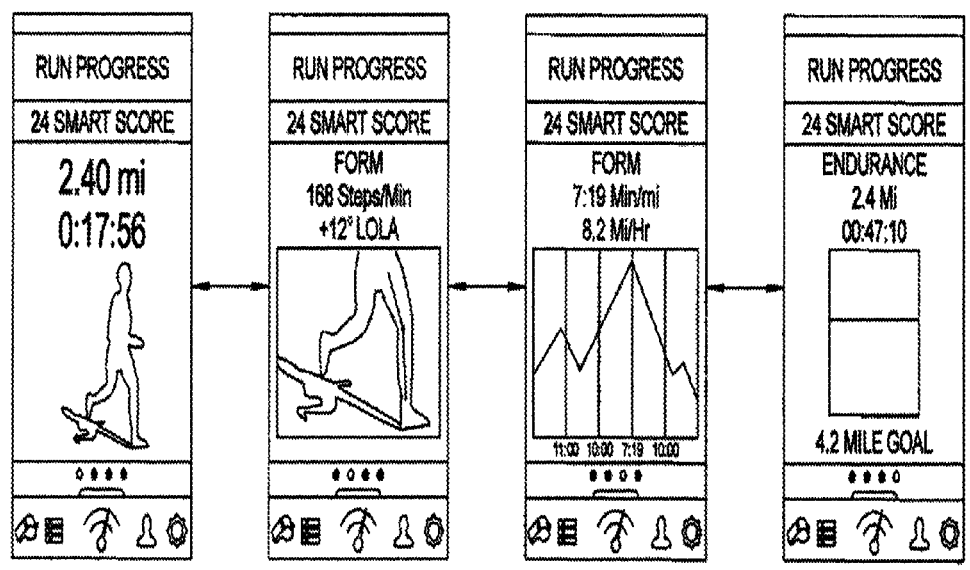
Figure 6:
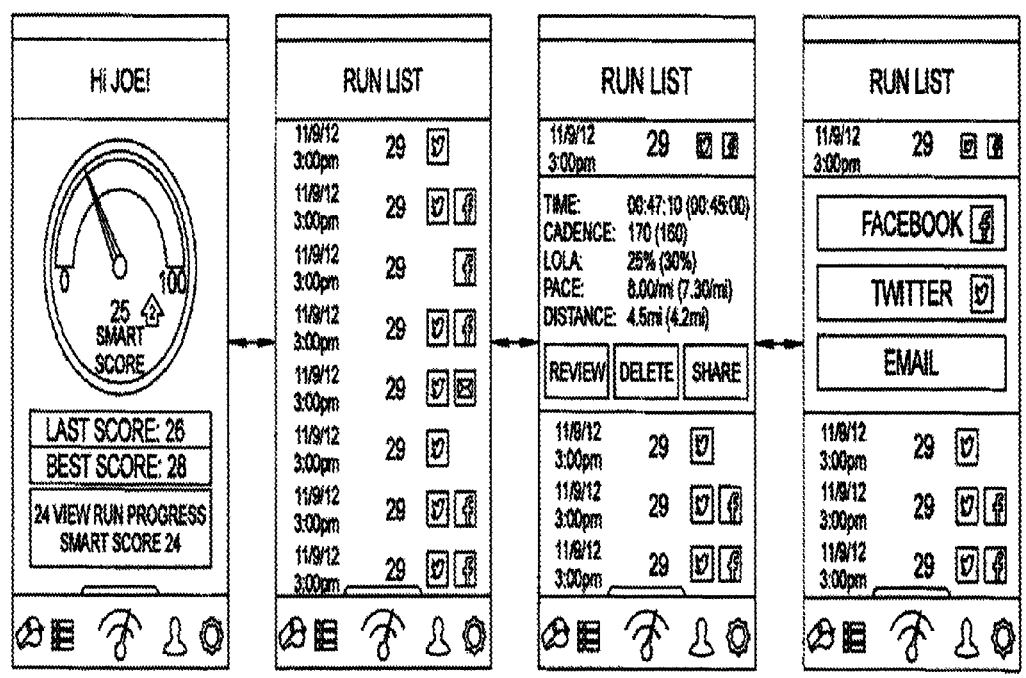

With reference to FIGS. 4 through 6, one embodiment of the use of the device in association with an outside computing device (in this case a smartphone) is shown. Specifically, when the smartphone application is launched for the first time (or when users change), the user is prompted to provide profile information. This information my include name, age, height, gender, desired units for output, among others. Once entered, the system prompts the user to put the device on his or her ankle (if the same has not yet been done). The device is then turned on. Once ready, the user starts the calibration process by running for a minute after hitting the start (or begin) button on the smartphone. The initial calibration provides the system with the general information as to the user's particular parameters during running Once calibrated, the device is ready for use.

The user can then start to walk or run. The device will sample the different sensors and provide the data, preferably wirelessly, to the smartphone. The smartphone application then processes the data, along with, for example, data from its own sensors (i.e., GPS, clock etc.) to provide output to the user. Among other data, the application can provide information pertaining to form (steps per minute, lower leg angle, time of foot contact), speed, and endurance. The information can be provided real-time to the user. It is contemplated that the information as to the instant condition can be displayed on the smartphone, and, if any of the parameters are outside of the desired range, an audible signal (or kinesthetic signal—vibration) can be triggered. The signals can be different and parameter dependent (as well as condition dependent) so that the user has the information necessary to understand not only which parameter, but the reason for the alert. The user can then take the appropriate action.

The system can, through a predetermined algorithm provide a score to the particular run during or after completion, to provide the user with an overall understanding of the quality of the run. Additionally, during the run, the system can audibly (or otherwise—vibration, lights, etc.) provide the user with information as to the current form or other problems that can be corrected by the user.

After a run is complete, the application can store the different completed runs (or training sessions). The data pertaining to the run can be transmitted to a remote computer (or server, or cloud storage system). Access can be provided to the data to, for example, a personal trainer, coach, etc.

That individual can analyze the data and provide feedback as to any number of different items. Furthermore, the user can share the scores and the different runs on social media sites.

Figure 8:
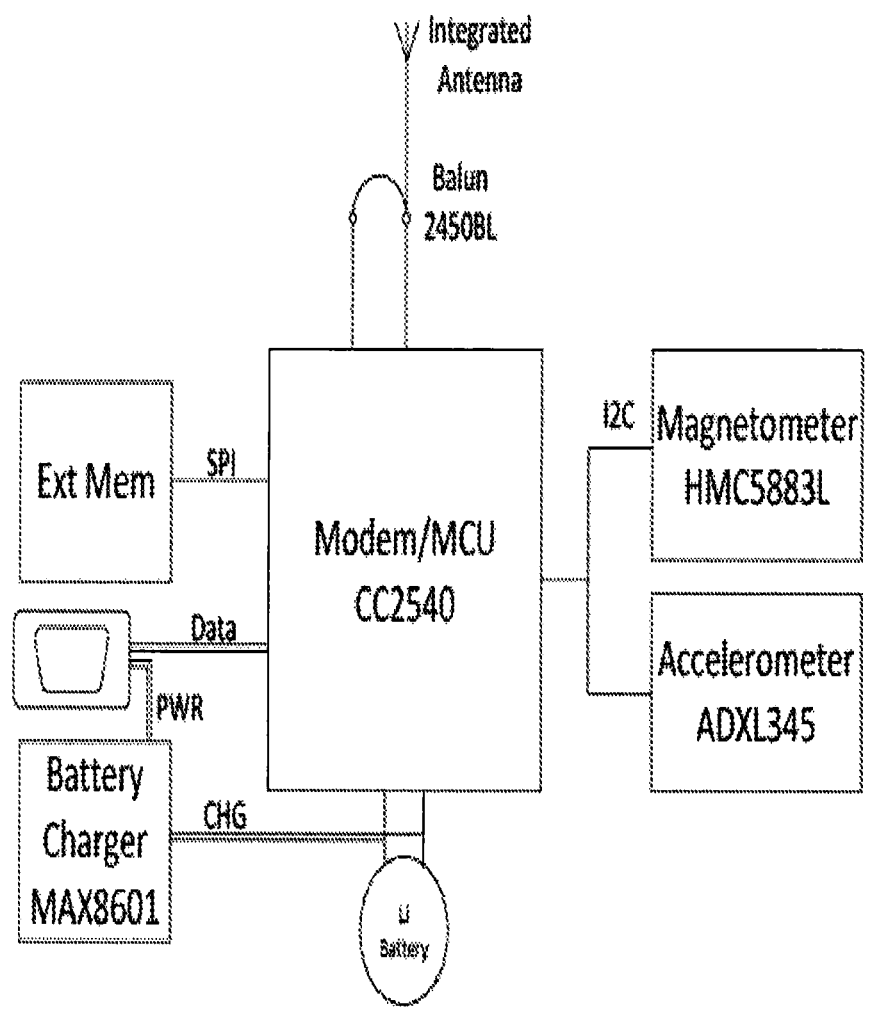

As previously described, the system can use an accelerometer to find the angle of the leg with respect to gravity. As shown in FIG. 8 a magnetometer and a fixed magnet can accurately determine the leg crossing point in the stride, which will harmonically discipline the accelerometer. The magnetometer was determined to be the best of several options, which included an ultrasound Doppler solution, inductive coupling, and a RF amplitude proximity sensor.

The magnetometer has the benefit of being an inexpensive, simple, and low power solution. The theory of operation is that a sensor will be attached to either ankle of the runner, facing inward. One sensor can have a small magnet, and the other can have a 3-axis magnetometer. Both sensors will include a 3-axis accelerometer, and can include a Blue Tooth Low-Energy transceiver, memory for data logging and a USB port for charging the battery and downloading collected data. The sensors perform basic data reduction and data logging; they are be able to communicate the data to a third device using a Blue Tooth Low Energy (BLE) protocol or USB. The sensors are battery powered, and rechargeable through a micro-USB connector.

As described, the accelerometers are able to determine position using a double integration, and small errors become cumulative over time. In order to overcome this problem, a means of nulling the drift in the accelerometer is preferably included in a viable sensor system. To accomplish the nullification of the drift, a magnetometer is used to accurately indicate the point at which one leg passes near the other. With this information, it is possible to operate the accelerometer as a harmonic measurement instrument and reconstruct the stride of the runner.

The system can be formed of several blocks: the magnet/magnetometer, the accelerometer, the communication and data-logging control, and the battery and battery charging circuitry. The data can be transmitted to a nearby computer through a wireless communication or wire for data logging. The product is understood to be a circuit that preferably: 1. provides an accelerometer measurement of sufficient accuracy and dynamic range to measure the form of the stride; 2. Provides a method to zero the drift in the accelerometer measurements; 3. Provides method to gather and log the data, (transmit to an data gathering device); 4. The cost of the sensor system is less than $40; 5. Powered for at least 4 hours of operation; and 6. Mountable on the ankle of the user.

Using a magnetometer to correct and to zero the drift in the accelerometers requires some analysis using a processor. The intensity and direction of the magnetic field about a permanent magnet, the selection of a magnet, how to detect the point in the stride where the ankles are nearest, and the selection of a magnetometer.

At a sufficient distance from the source, a permanent magnet may be approximated as a dipole. The magnetic flux density about the magnetic moment is given by: Where is the magnetic dipole moment, is the spherical radial coordinate, denotes the unit vector of the direction, and is the free space magnetic permeability. The strength of commercial permanent magnet is specified in residual flux density, or residual induction. The residual induction is specified according to the flux on the axis of a cylindrical magnet: where is the length of the magnet, is the radius of the cylinder, and is the coordinate of the axis of the cylinder. To convert residual flux density to magnetic dipole moment, we consider the dominate functional component for.

At a sufficient distance from the source, a permanent magnet may be approximated as a dipole. The magnetic flux density about the magnetic moment is given by:

$$\bar{B}(\bar{r}) = \frac{m\mu_0}{4\pi r^3}(3\hat{r}(\hat{m}\cdot\hat{r}) - \hat{m})$$

Where m is the magnetic dipole moment, r is the spherical radial coordinate, ^ denotes the unit vector of the direction, and $mu_0$ is the free space magnetic permeability.

$$B_z(z) = \frac{B_r}{2}\left(\frac{L+z}{\sqrt{R^2+(L+z)^2}} - \frac{z}{\sqrt{R^2+z^2}}\right)$$

The strength the of commercial permanent magnet is specified in residual flux density, or residual induction. The residual induction is specified according to the flux on the axis of a cylindrical magnet:
where L is the length of the magnet, R is the radius of the cylinder, and Z is the coordinate of the axis of the cylinder. To convert residual flux density to magnetic dipole moment, we consider the dominate functional component for $Z \gg L, R$.

FIG. 8 a schematic of the system according to the present teachings having magnetometer and accelerometer. Shown is a process couples to external memory and a power supply. Additionally coupled to the processor is a magnetometer and a tri-axial accelerometer.

Figure 9:
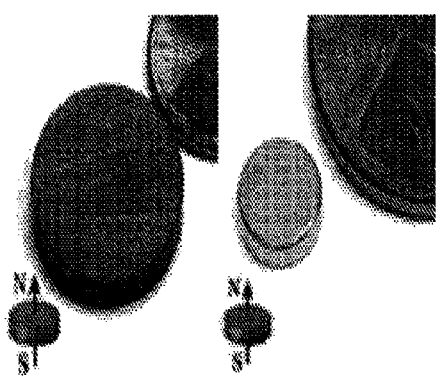
FIG. 9 depicts the fixed magnet usable in the system according to the present teachings.

FIG. 9 depicts the fixed magnet usable in the system according to the present teachings the magnets can have the following properties:

| Different ceramic materials have different residual flux densities. The cheapest magnets are made from hard ferrite ceramics. The strongest magnets are made from neodinium-iron-boron Material and Grade | Residual Flux Density, Br | Flux at distance of 0.050" from surface of magnet |
|---|---|---|
| Ceramic 1 | 2,200 | 629 |
| Ceramic 5 | 3,950 | 1,130 |
| SmCo 18 | 8,600 | 2,460 |
| SmCo 26 | 10,500 | 3,004 |
| NdFeB 35 | 12,300 | 3,518 |
| NdFeB 42H | 13,300 | 3,804 |

Figure 10:
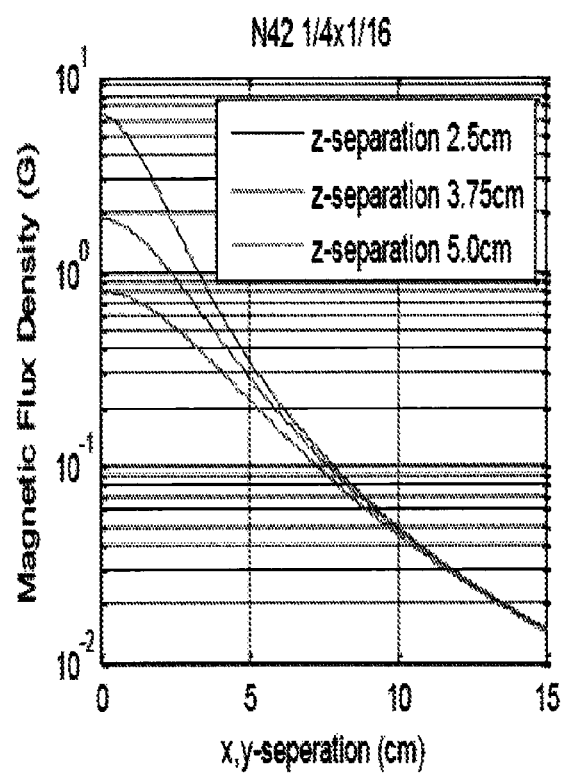
FIG. 10 represents a measures magnetic flux density at x,y separation from the detector according to the present teachings.

In North America, the Earth's magnetic field is typically around 0.2 G and does not exceed 0.3 G. This component can be removed through a primitive spectral analysis that captures only the time-harmonic portions of the varying magnetic field. Typical magnetometers have a dynamic range of ±8 G. As the intensity of the measured magnetic field is such a strong function of the distance from the magnet, determining the point at which the ankles are nearest is a well-conditioned problem. The magnitude of the magnetic flux density as a function of z-separation and x/y displacement is shown in FIG. 10. The coordinate system is shown in FIG. 9.

Optionally, the Honeywell HMC5883L magnetometer for this application. It is a 3-axis, low-noise, 12-bit magnetometer with an ±8 G dynamic range that costs approximately $1.50 in quantity. The magnetometer is compatible with a simple 2-wire $I_2C$ interface. The accelerometer, can be the Analog Devices ADXL345. It is a 3-axis accelerometer with 16-bit resolution and a ±16 g dynamic range. It is compatible with standard 2-wire $I_2C$ interfaces, is widely commercially available, and has minimal development risks.

Communication and processing can be accomplished using a TI CC2540F256 Blue Tooth Low Energy modem with integrated 8051 microcontroller and 256K flash memory. This single part will satisfy the requirements for both a microprocessor and a modem. We recommend using a printed inverted-F matched to 2.4-2.5 GHz band through a Johansson 2450BL Bluetooth Balun. Depending upon the final size constraints, the printed antenna may be altered for a less efficient, but smaller chip antenna. The CC2540 is USB compatible for communication.

The device be powered using a 3V rechargeable 100 mAh coin cell. The battery will be recharged using a Max8601 Li-Ion battery charger which is designed to fully and safely charge lithium batteries from a USB power source. Based upon preliminary estimates, a 100 mAh should provide at least 4 hours of operation.

Figure 11:
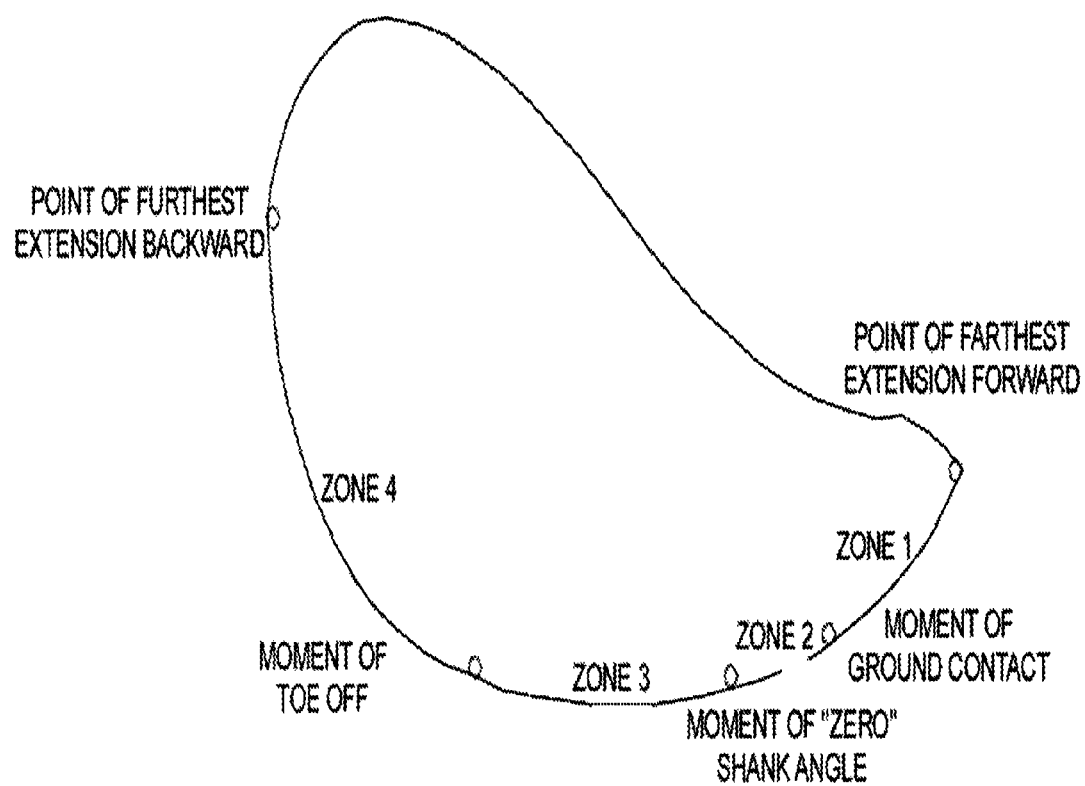
FIG. 11 represents a generic runner's stride as measured by the present system.

FIG. 11 represents a generic runner's stride as measured by the present system. Starting at a strides furthest extension 30. The segment between the furthest extension 30 and the moment the foot makes contact with the ground is defined as zone 1. Between the moment of ground contact and the point the runner's shank angle is at "zero" shank angle is defined as zone two. As the foot is pulled back toward the runner. Zone three is defined between the zero shank angle and the moment the toe leaves the ground. Zone four is defined between the time or point the toe leaves the ground to the point of furthest backward extension. The system is configured to reduce the size of zone two for all runner's strides.

Figure 12:
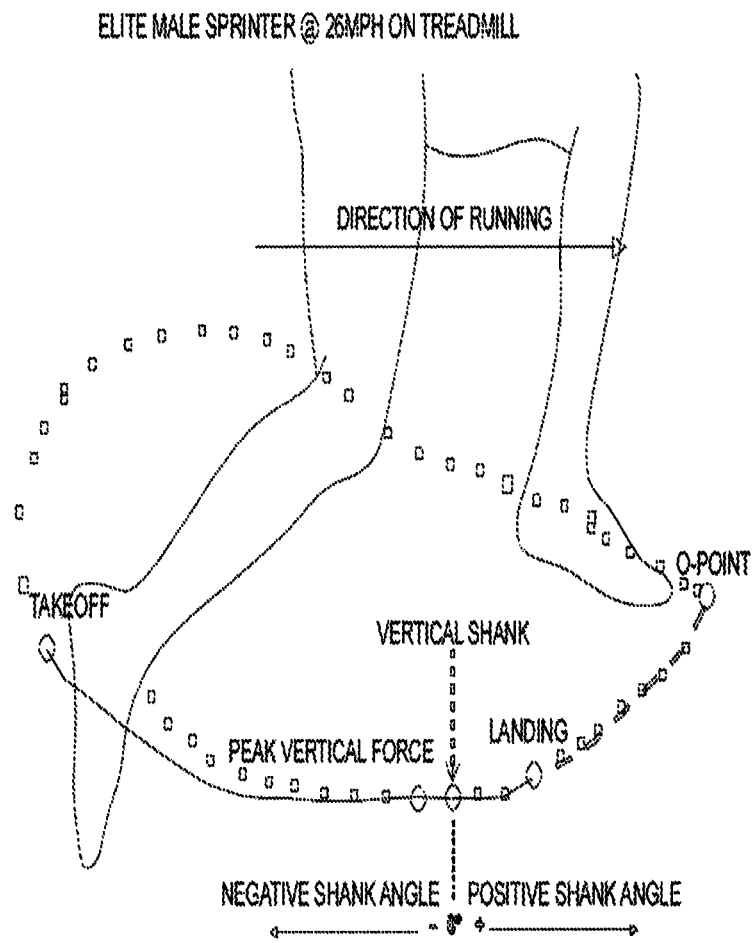
FIG. 12 represents the stride of an elite male sprinter.

FIG. 12 represents the stride of an elite male sprinter. Shown are not only the points of zones one through zone four. As can be seen, the peak vertical force for an elite male sprinter is after zone two or when the shank angle passes through zero.

Figure 13:
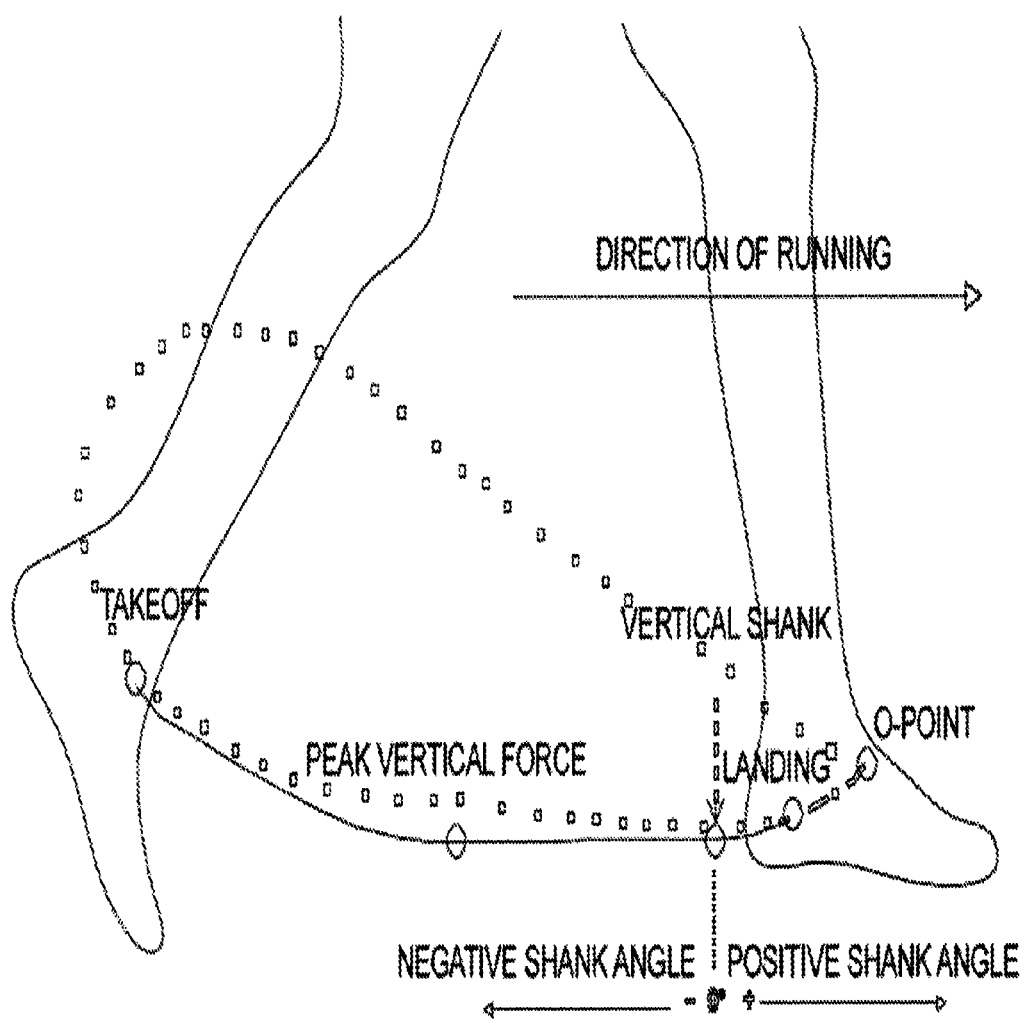
FIG. 13 represents the stride of a first user having a rearfoot strike.

FIG. 13 represents the stride of a first user having a rearfoot strike. Shown are not only the points of zones one through zone four. As can be seen, the peak vertical force for an runner who has a rear foot strike is within zone two or before the shank angle passes through zero. A second force peak was developed within the third zone.

Figure 14:
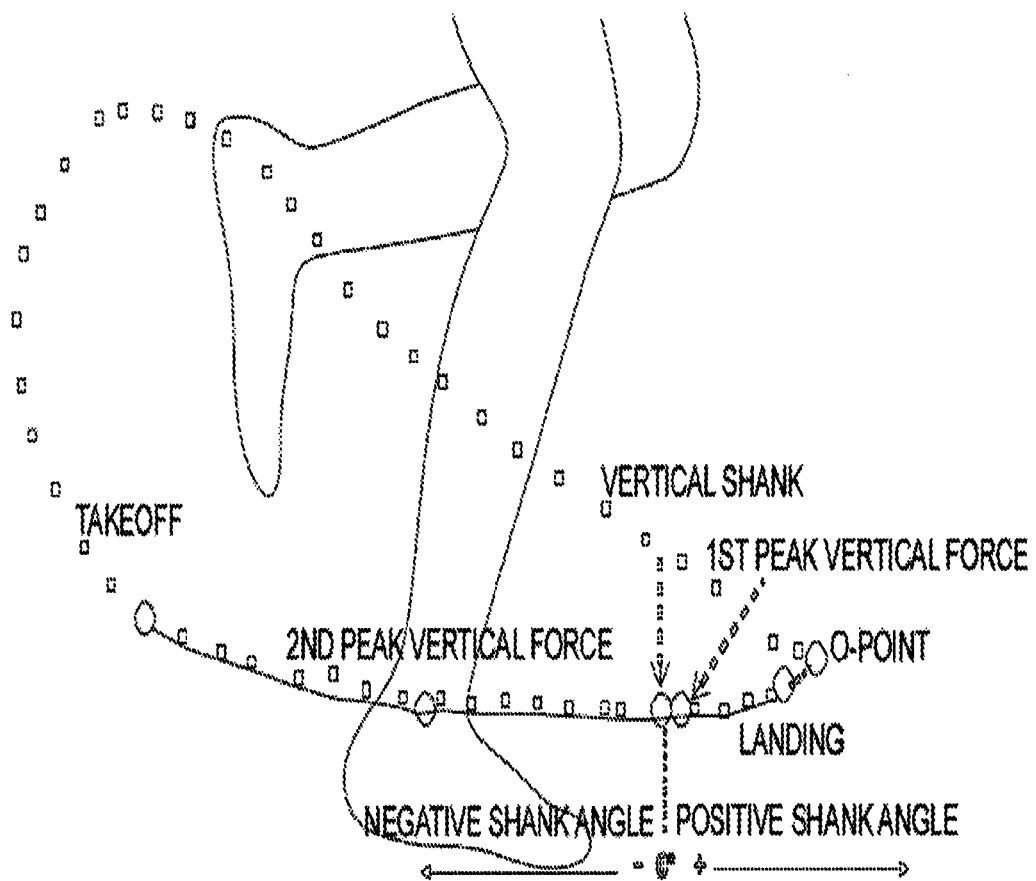
FIG. 14 represents the stride of a second user having a rearfoot strike.

FIG. 14 represents the stride of a second user having a rearfoot strike. Shown are not only the points of zones one through zone four. As can be seen, the peak vertical force for an runner who has a rear foot strike is within zone two or before the shank angle passes through zero. A second force peak was developed within the third zone.

FIG. 15 represents the stride of a third user having a rearfoot strike. As shown in the Time vs Force graph, the heal strike stride presents a shock zone where the runner is breaking or slowing down, prior to the shank angle of zero. A second peak is reached within zone three after the shank angle is zero.

Figure 16:
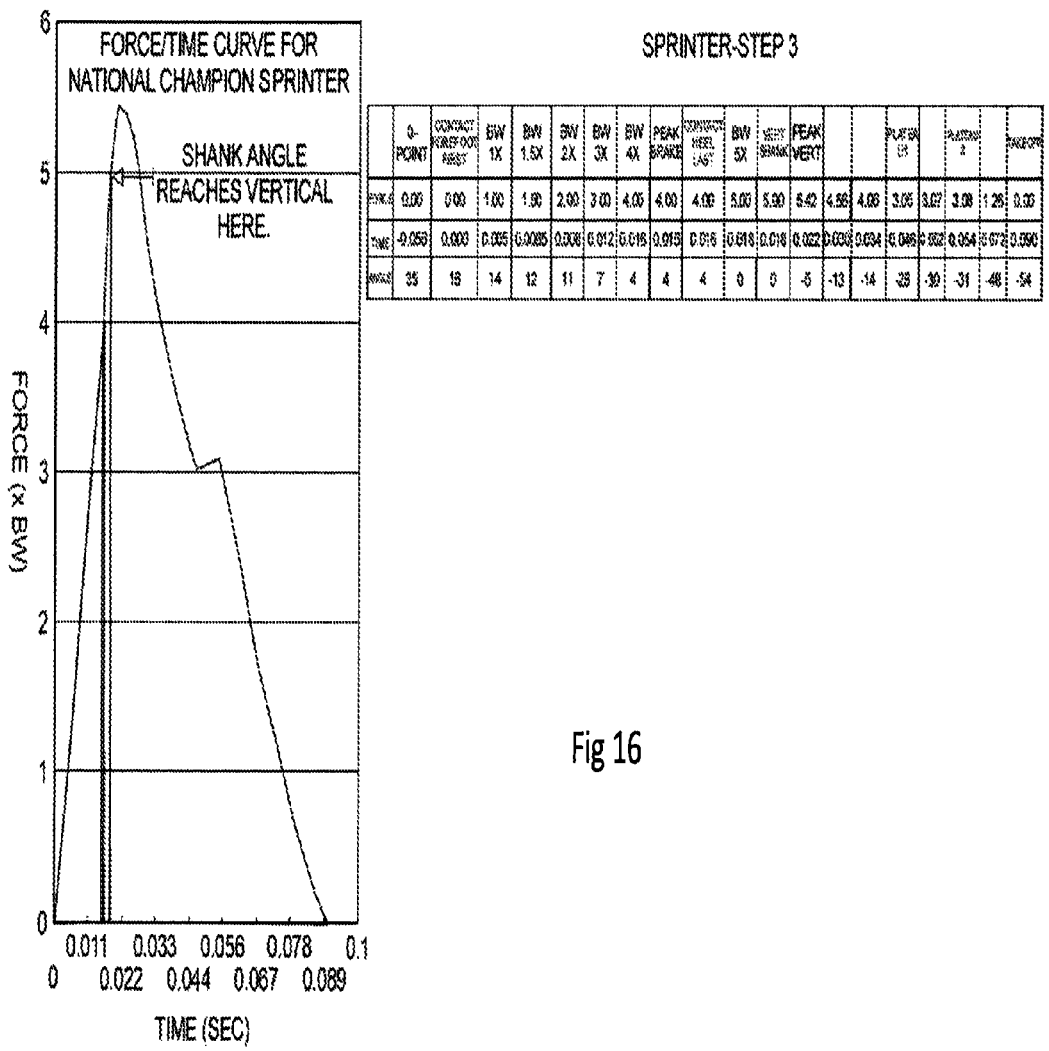
FIG. 16 represents force vs. time data for the stride of a user having a forefoot strike.
Figure 18:
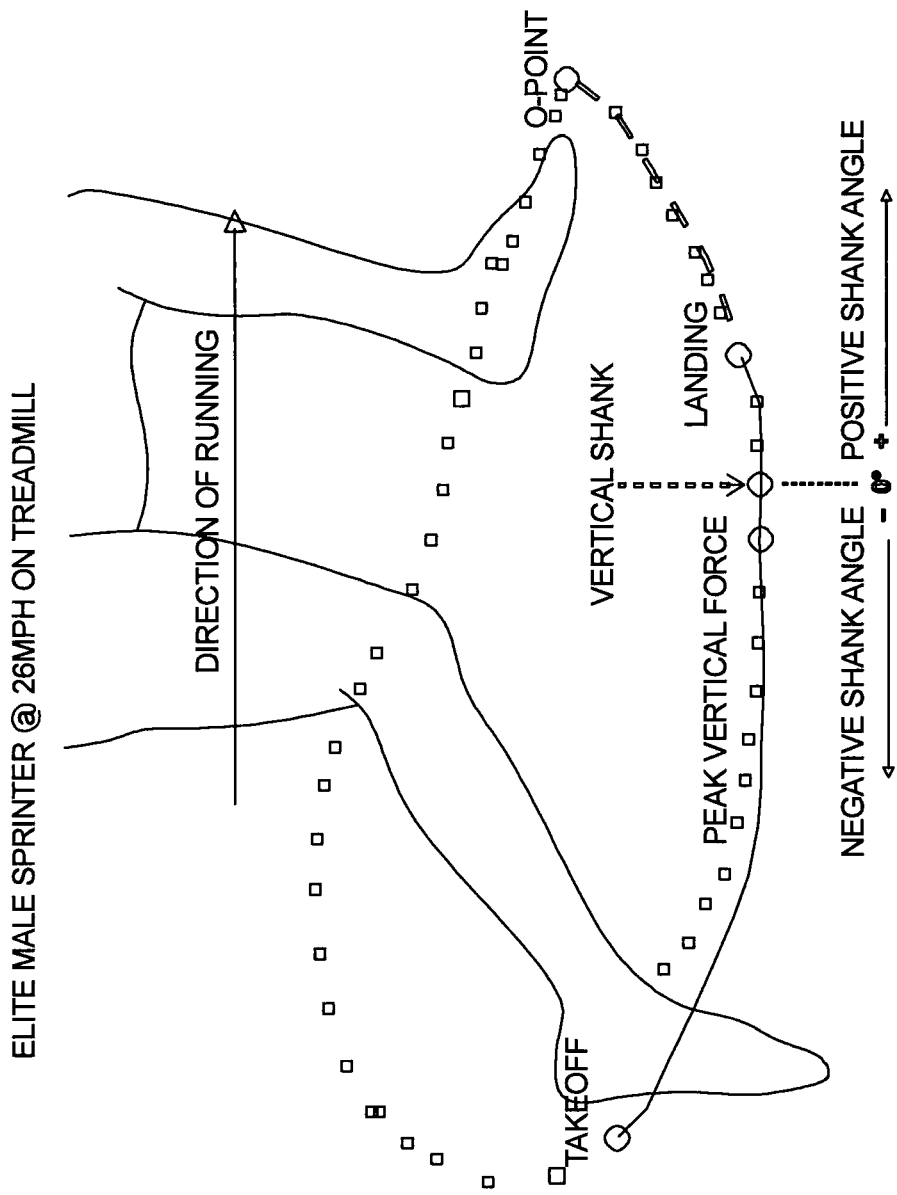
FIG. 18 represents displacement vs. impact data for the stride of a user having a forefoot strike.
Figure 19:
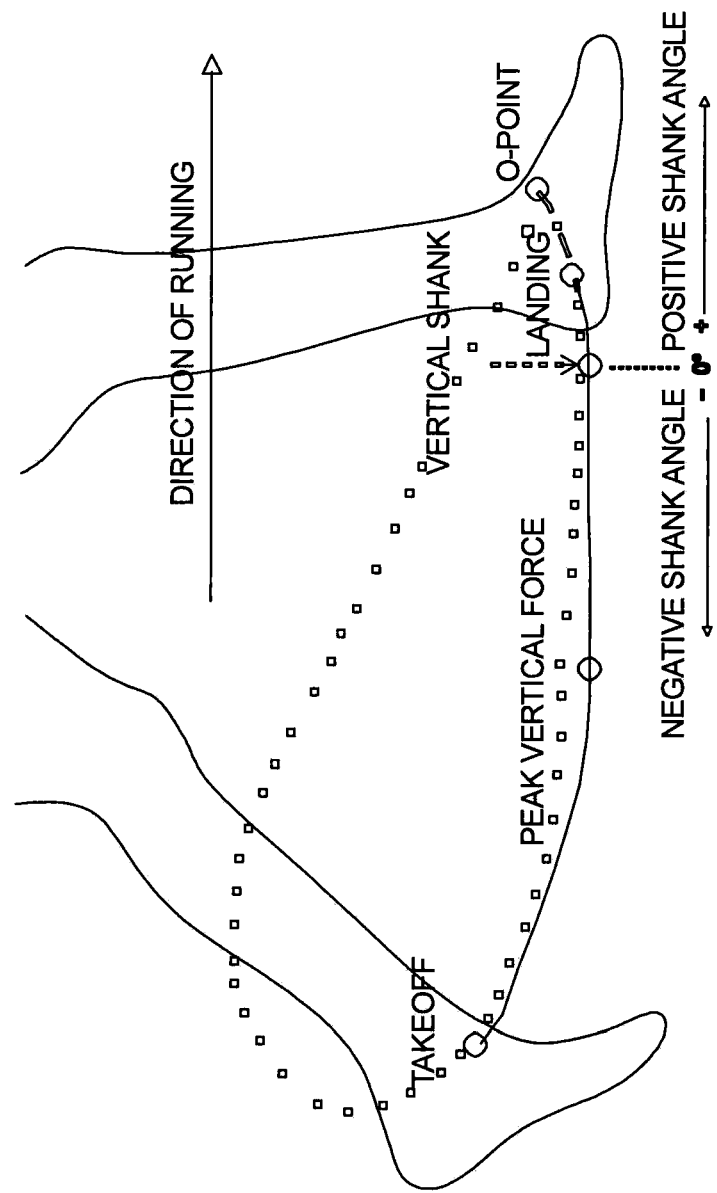
FIG. 19 represents displacement vs. impact data for the stride of a user having a forefoot strike.
Figure 20:
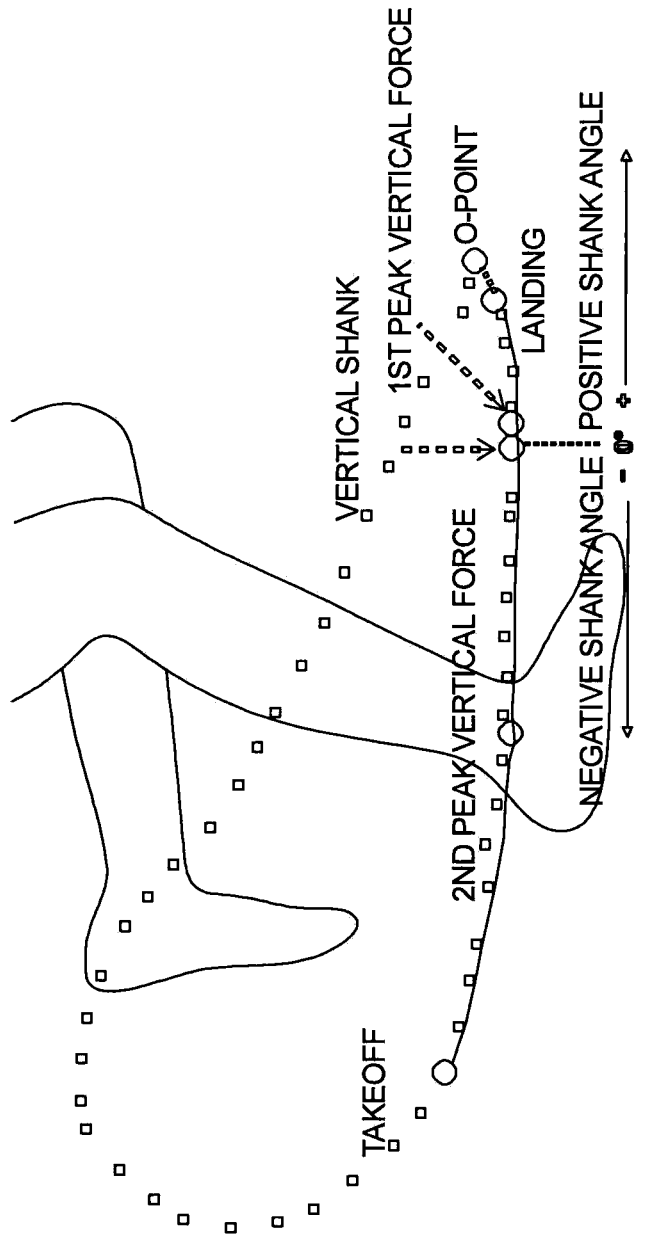
FIG. 20 represents displacement vs. impact data for the stride of a user having a rearfoot strike.

FIG. 16 represents force vs. time data for the stride of a sprinter having a forefoot strike. As can be seen, there is no deleterious shock zone which may be the cause of damage to runner's knees and ankles. FIG. 17 represents force vs. time data for the stride of a user having a forefoot strike. As shown, the brake zone occurs but the deleterious force spike does not appear prior to the vertical shank angle. FIGS. 18, 19, and 20 represent displacement vs. impact data for the stride of a Elite male sprinter, a forefoot striking runner, and rearfoot striking runner. Shown are the first, second third, and fourth zone.

Figure 21:
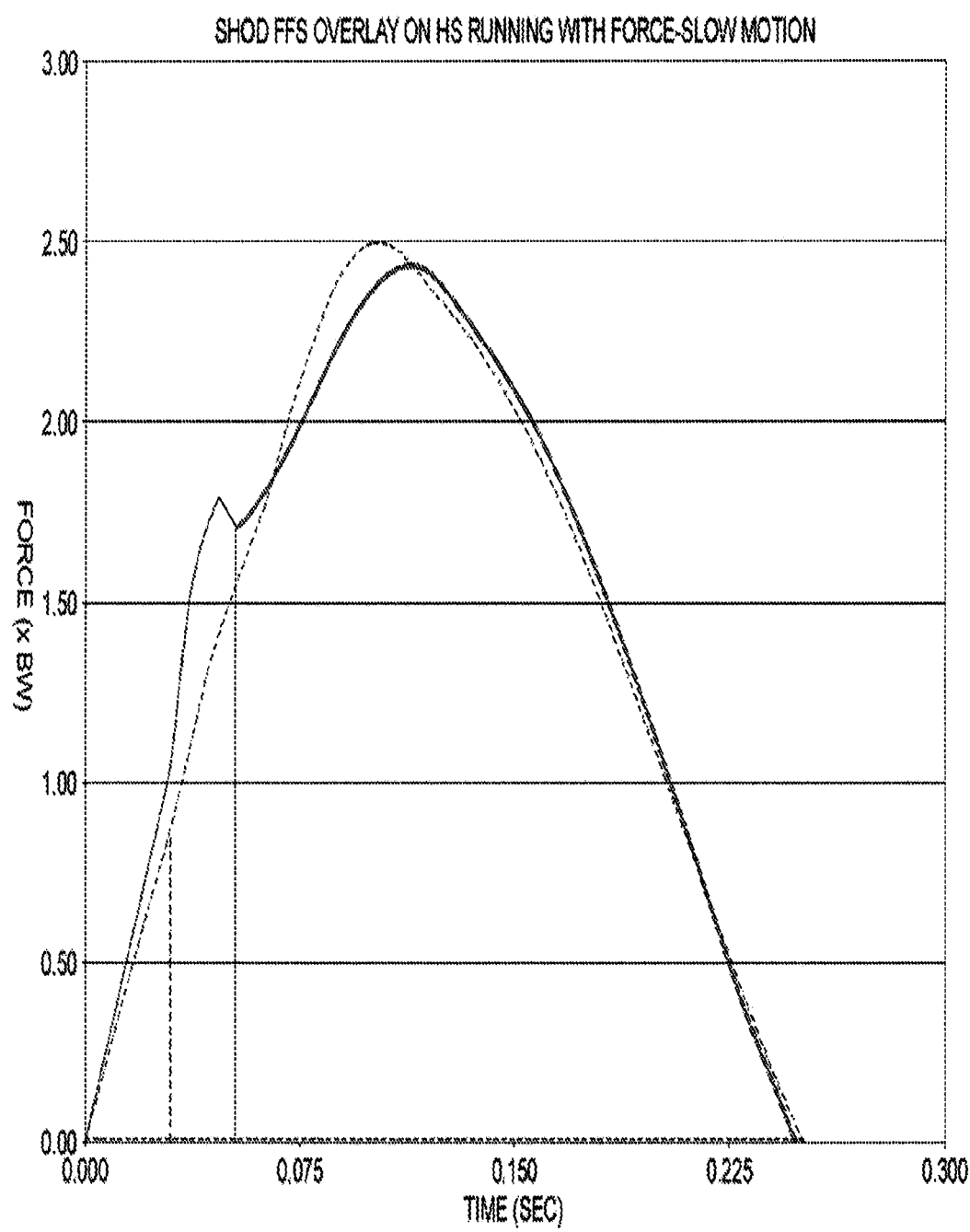
FIG. 21 represents the comparison for vs. impact data for the stride of a user having a rearfoot and forefoot strike.

FIG. 21 represents the comparison force vs. impact data for the stride of a user having a rearfoot and forefoot strike. As shown, the solid line represents a heal strike runner having a high sharp impact load in zone one and prior to the zero shank angle. This is opposed to the dashed line where the fore foot engagement does not have the deleterious high impact load.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A method of providing data to a user that is running or walking comprising the steps of:
    providing a lower leg sensing device having a mounting member configured to mount the lower leg sensing device on a user leg between the user's knee and ankle, the lower leg sensing device including at least a position angle sensor configured to measure a shank angle of the user at a time of a foot contact and a foot contact sensor and a magnetic field measurement system configured to measure a magnet positioned on a user leg;
    coupling the lower leg sensing device to a lower leg of a user between the user's knee and ankle;
    sampling the position angle sensor and the foot contact sensor;
    determining the angle of the lower leg relative to a line of gravity based upon the data received from the position angle sensor and the foot contact sensor;
    providing information to a user pertaining to the angle of the lower leg relative to the line of gravity;
    comparing the angle that has been determined to a known range of acceptable angles using a program module;
    providing a user understandable signal to a user sufficient for the user to determine whether the angle that has been determined is within the known range of acceptable angles;
    providing a first user understandable signal if the angle that has been determined is within the known range of acceptable angles;
    providing a second user understandable signal if the angle that has been determined is outside of the known range of acceptable angles on a first side of the range.

2. The method of claim 1 wherein the first and second understandable signals comprise at least one of audible, visual and kinesthetic signals.

3. The method of claim 1 further comprising the steps of:
    providing a computing device that is separated from the sensing device;
    establishing a communication link between the computing device and the sensing device; and
    transmitting data obtained through sampling of the position angle sensor and the foot contact sensor.

4. The method of claim 3 further comprising the step of:
    displaying in real-time on the computing device the data obtained through sampling of the position angle sensor and the foot contact sensor.

5. The method of claim 3 wherein the computing device comprises a communication device coupled wirelessly to the sensing device, and the step of displaying comprises the step of displaying on a display of the communication device.

6. The method of claim 5 wherein the communication device further includes a GPS sensor and further includes a clock, the method further comprising the step of:
    computing at least one other parameter based upon the sensors, including, at least one of cadence, speed, time, stride length, and ground contact time.

7. The method of claim 1 wherein the lower leg sensing device further includes:
    a first housing, wherein the position angle sensor and the foot contact sensor are positioned therewithin; and
    a leg attachment member configured to releasably attach the housing to the lower leg of the user above the user's ankle.

8. The method of claim 7 wherein the lower leg sensing device further includes:
    a second housing, wherein the magnet is positioned therewithin.

9. A lower leg sensing device for measuring a lower angle between a user's knee and ankle, the lower leg sensing device comprising:
    a position angle sensor, a magnetic field sensor and a foot contact sensor;
    a leg attachment member configured to facilitate attachment of the position angle sensor and a foot contact sensor to the lower leg of a user above the user's ankle; and
    a module configured to provide real-time data pertaining to the angle of a lower leg of a user relative to a line of gravity impact of a foot with a ground surface by the user, said module further being configured to comparing the angle that has been determined to a known range of acceptable angles using a program module and provide a user understandable signal to a user sufficient for the user to determine whether the angle that has been determined is within the known range of acceptable angles and compare changes in a measured magnetic field to determine if a stride has been taken, and further provide a first user understandable signal if the angle that has been determined is within the known range of acceptable angles, and further provide a second user understandable signal if the angle that has been determined is outside of the known range of acceptable angles on a first side of the range.

10. The lower leg sensing device of claim 9 wherein module configured to provide real-time data further comprises:
    first module wirelessly coupled to the position angle sensor and the foot contact sensor;
    a signal member coupled to the first module, the signal member capable of providing a user understandable signal.

11. The lower leg sensing device of claim 10 wherein the at least one user understandable signal comprise at least one of audible, visual and kinesthetic signals.

12. The lower leg sensing device of claim 11 wherein the first module further comprises a communication device and wherein the signal member comprises at least one of the display of the communication device, a speaker of the communication device and a vibration mechanism of the communication device.

* * * * *